(12) United States Patent
Branch et al.

(10) Patent No.: US 7,556,601 B2
(45) Date of Patent: Jul. 7, 2009

(54) SYSTEMS AND TECHNIQUES FOR ILLUMINATING A SURGICAL SPACE

(75) Inventors: Charles L. Branch, Advance, NC (US); Kevin T. Foley, Germantown, TN (US); Maurice M. Smith, Cordova, TN (US); Thomas E. Roehm, III, Braden, TN (US); Richard Franks, Memphis, TN (US)

(73) Assignee: Warsaw Orthopedic, Inc.

( * ) Notice: Subject to any disclaimer, the term of this patent is extended or adjusted under 35 U.S.C. 154(b) by 1006 days.

(21) Appl. No.: 10/633,288

(22) Filed: Aug. 1, 2003

(65) Prior Publication Data
US 2004/0143169 A1 Jul. 22, 2004

Related U.S. Application Data

(60) Provisional application No. 60/400,562, filed on Aug. 2, 2002.

(51) Int. Cl.
*A61B 1/32* (2006.01)
(52) U.S. Cl. ..................... 600/245
(58) Field of Classification Search ........... 600/201, 600/210, 212, 219, 220, 223, 235, 237, 241, 600/245, 108; 606/1–2, 7, 13–16; 362/551, 362/556, 558, 572–574
See application file for complete search history.

(56) References Cited

U.S. PATENT DOCUMENTS

| | | | |
|---|---|---|---|
| 1,326,300 A | 12/1919 | Smit | |
| 2,235,979 A | 3/1941 | Brown | |
| 3,261,350 A | 7/1966 | Wallace | |
| 3,384,076 A * | 5/1968 | Speelman | 600/200 |
| 3,564,231 A * | 2/1971 | Bruce et al. | 362/558 |
| 3,590,232 A | 6/1971 | Sadowski | |
| 3,592,199 A * | 7/1971 | Ostensen | 600/198 |
| 3,626,471 A * | 12/1971 | Florin | 600/205 |
| 3,664,330 A | 5/1972 | Deutsch | |
| 3,680,546 A * | 8/1972 | Asrican | 600/219 |
| 3,796,214 A * | 3/1974 | Davis | 600/205 |
| 3,807,393 A * | 4/1974 | McDonald | 600/208 |
| 4,086,919 A * | 5/1978 | Bullard | 600/188 |
| 4,173,392 A | 11/1979 | Ekinaka et al. | |
| 4,295,465 A * | 10/1981 | Racz et al. | 600/192 |
| 4,500,181 A | 2/1985 | Takahashi | |
| 4,562,832 A | 1/1986 | Wilder et al. | |
| 4,597,030 A | 6/1986 | Brody et al. | |
| 4,627,421 A * | 12/1986 | Symbas et al. | 600/232 |
| 4,802,460 A | 2/1989 | Ohkuwa et al. | |
| 4,905,082 A | 2/1990 | Nishigaki et al. | |
| 4,907,132 A | 3/1990 | Parker | |
| 4,947,896 A * | 8/1990 | Bartlett | 600/187 |
| 5,005,108 A * | 4/1991 | Pristash et al. | 362/602 |
| 5,039,198 A | 8/1991 | VanBeek | |

(Continued)

FOREIGN PATENT DOCUMENTS

EP  0 566 359 A2  10/1993

(Continued)

*Primary Examiner*—Anu Ramana

(57) ABSTRACT

Methods and devices for illuminating a surgical space during surgery in a patient are provided. A retractor provides a working path for access to a location in the patient. A light instrument is positionable in working channel to emit light at the surgical space without substantially obstructing access to the surgical space.

31 Claims, 2 Drawing Sheets

U.S. PATENT DOCUMENTS

| | | | |
|---|---|---|---|
| 5,165,387 A | 11/1992 | Woodson | |
| 5,170,454 A * | 12/1992 | Kanai | 385/88 |
| 5,293,863 A * | 3/1994 | Zhu et al. | 600/214 |
| 5,334,150 A | 8/1994 | Kaali | |
| 5,353,786 A | 10/1994 | Wilk | |
| 5,354,302 A | 10/1994 | Ko | |
| 5,381,787 A * | 1/1995 | Bullard | 600/188 |
| 5,400,773 A | 3/1995 | Zhu et al. | |
| 5,441,041 A | 8/1995 | Sauer et al. | |
| 5,445,142 A | 8/1995 | Hassler, Jr. | |
| 5,448,990 A | 9/1995 | De Faria-Correa | |
| 5,562,696 A | 10/1996 | Nobles et al. | |
| 5,584,796 A | 12/1996 | Cohen | |
| 5,588,949 A | 12/1996 | Taylor et al. | |
| 5,588,951 A | 12/1996 | Zhu et al. | |
| 5,591,192 A | 1/1997 | Privitera et al. | |
| 5,603,688 A * | 2/1997 | Upsher | 600/190 |
| 5,630,795 A | 5/1997 | Kuramoto et al. | |
| 5,759,150 A | 6/1998 | Konou et al. | |
| 5,785,648 A | 7/1998 | Min | |
| 5,802,227 A * | 9/1998 | Dunn et al. | 385/53 |
| 5,817,005 A | 10/1998 | Cohen | |
| 5,891,013 A | 4/1999 | Thompson | |
| 5,967,971 A | 10/1999 | Bolser | |
| 6,129,662 A | 10/2000 | Li et al. | |
| 6,139,493 A | 10/2000 | Koros et al. | |
| 6,176,824 B1 | 1/2001 | Davis | |
| 6,185,356 B1 * | 2/2001 | Parker et al. | 385/133 |
| 6,196,968 B1 | 3/2001 | Rydin et al. | |
| 6,210,325 B1 | 4/2001 | Bartie et al. | |
| 6,234,656 B1 * | 5/2001 | Hosseini et al. | 362/556 |
| 6,304,712 B1 | 10/2001 | Davis | |
| 6,427,034 B1 | 7/2002 | Meis et al. | |
| 6,585,727 B1 * | 7/2003 | Cashman et al. | 606/16 |
| 6,621,966 B2 * | 9/2003 | Lail | 385/114 |
| 2002/0080248 A1 | 6/2002 | Adair et al. | |

FOREIGN PATENT DOCUMENTS

GB    2 133 694    8/1994

* cited by examiner

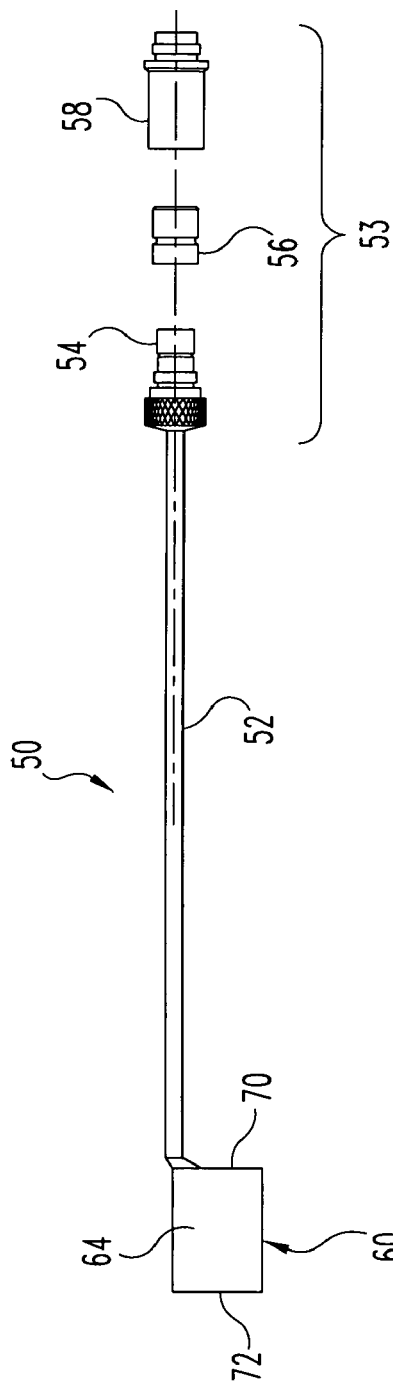
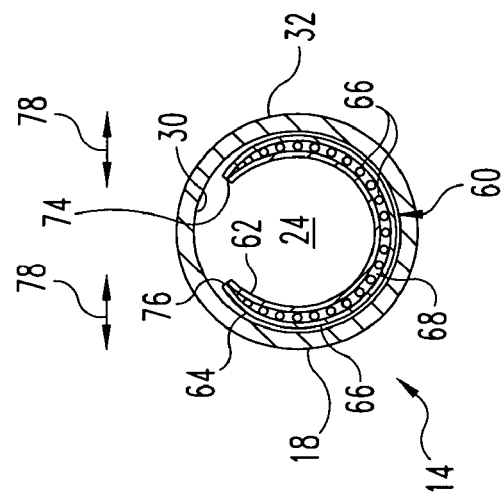
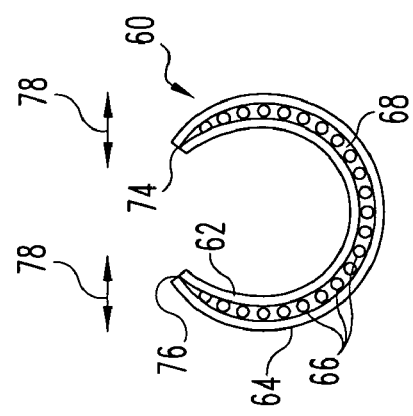

SYSTEMS AND TECHNIQUES FOR ILLUMINATING A SURGICAL SPACE

CROSS-REFERENCE TO RELATED APPLICATION

This application claims the benefit of the filing date of Provisional Application Ser. No. 60/400,562 filed on Aug. 2, 2002.

BACKGROUND

A surgical space in a patient can require illumination for the surgeon to properly perform surgical procedures in the surgical space. In minimally invasive procedures, a second portal can be provided so that a light can be positioned at the surgical space through the second portal. A light could be inserted through the same portal used by the surgeon to access the space. Also, a light could be located above the portal.

The use of such lights has several drawbacks. For example, the use of a second portal increases the invasiveness of the procedure. Positioning a light instrument through a common access portal occupies space along the working channel, making it more difficult for the surgeon to maneuver instruments in the surgical space working channel, or requiring an increase in the size of the portal and thus increasing the invasiveness of the procedure. Also, the light may be secured to the portal during the procedure, which can obstruct access to or visualization of the surgical space through the portal.

It would be desirable to provide illumination of a surgical space in a minimally invasive surgical procedure while avoiding any one or combination of the aforementioned drawbacks. The present invention is directed to meeting this need, among others.

SUMMARY

According to one aspect, a system includes a retractor and a light instrument positionable in the working channel of the retractor, wherein the light instrument is supported in the working channel by engagement with an inner wall surface of the retractor.

According to another aspect, a system includes a retractor coupled to a light instrument. The light instrument is deformable to assume any one of a number of configurations for positioning in the retractor working channel in contact with the inner wall surface thereof.

According to another aspect, a system includes a retractor coupled to a light instrument. The light instrument is engageable with an inner wall surface of the retractor working channel and movable along the inner wall surface in contact therewith to reposition the light instrument relative to the retractor.

According to another aspect, a system includes a retractor and a light instrument engageable to the retractor in the working channel. The light instrument includes a semi-circular body and a plurality of light transmitting elements spaced about a distal end thereof.

According to one aspect, a system includes a retractor and a light instrument positionable in the working channel of the retractor with a plurality of light transmitting elements spaced about the retractor working channel adjacent the inner wall surface.

These and other aspects, forms, features, objects, and advantages will also be apparent from the following description of the illustrated embodiments.

BRIEF DESCRIPTION OF THE FIGURES

FIG. 2 is a perspective view of a light instrument comprising a portion of the system of FIG. 1.

FIG. 3 is an end view of the light instrument of FIG. 2.

FIG. 4 is a sectional view through a retractor having the light instrument of FIG. 2 engaged thereto.

DESCRIPTION OF THE ILLUSTRATED EMBODIMENTS

Figure 1:
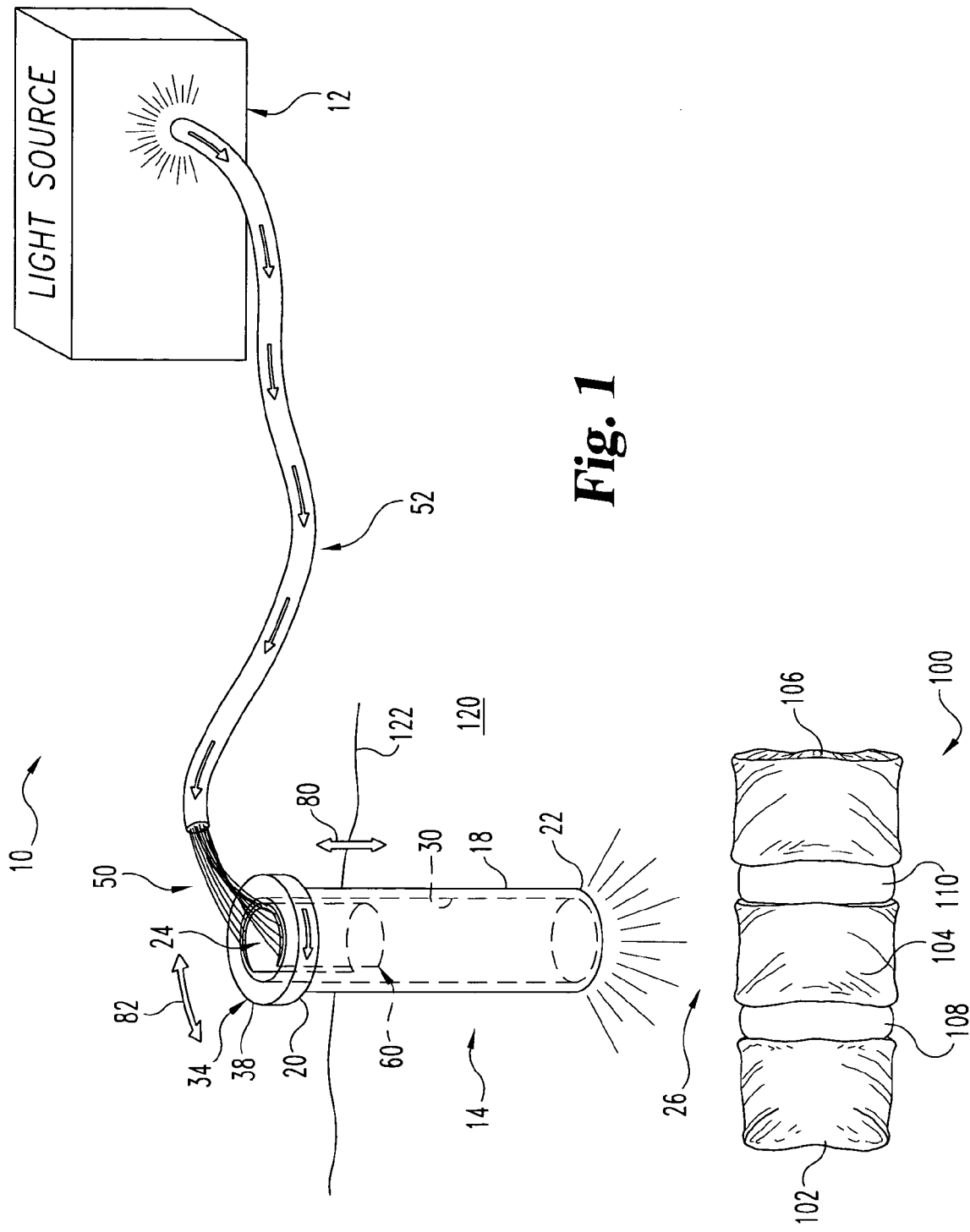
FIG. 1 is a perspective view of a retractor and light delivery system.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and described methods, and such further applications of the principles of the invention as illustrated therein being contemplated as would normally occur to one skilled in the art to which the invention relates.

The present invention provides instruments and methods for performing surgery, including minimally invasive surgery, in spinal applications such as laminotomy, laminectomy, foramenotomy, facetectomy, discectomy, positioning of interbody implants, positioning of intrabody implants, bone cutting and removal, tissue cutting and removal, and nerve root and tissue retraction, for example. Although the use of multiple portals is not precluded, also contemplated is the use of a single portal within the patient to perform surgical procedures. Systems and methods for providing light to the surgical space accessed by the surgeon through the portal are provided.

Referring to FIG. 1, there is shown a surgical system 10 that includes a light source 12 and a light instrument 50 coupled thereto. Light source 12 provides light through light instrument 50 to a retractor 14. The light is transmitted from light source 12 and into retractor 14, where it is emitted from light instrument 50 to illuminate the surgical space, including the working channel along retractor 14 and/or the working space adjacent the distal end of retractor 14. It is contemplated that body 18 can be made from light transmittable material such as glass or plastic, or an opaque material that does not transmit light.

Retractor 14 includes a body 18 extending between a proximal end 20 and a distal end 22. Body 18 can define a working channel 24 therethrough extending between and opening at proximal end 20 and distal end 22. Proximal coupling portion 34 can include a ring portion 38 extending about the proximal end of retractor 14. Working channel 24 can be sized to receive one or more surgical instruments therethrough to perform surgical procedures at working space 26 adjacent distal end 22 of retractor 14.

Retractor 14 can be inserted over the last of one or more tissue dilators and/or guidewires sequentially positioned one around the other to gradually retract tissue 120 and skin 122 of the patient. With retractor 14 positioned through the skin and tissue, the dilators are removed to provide access to working space 26 through working channel 24. In the illustrated embodiment, working space 26 is adjacent the spinal column segment 100. Working space 26 can include, for example, paraspinous tissue; the bony tissue of one or more of the vertebrae 102, 104, 106; the annulus tissue of disc space 108 between vertebrae 102, 104 and/or disc space 110 between vertebrae 104, 106; and/or a void created by manipulating tissue.

As further shown in FIG. 2, light instrument 50 includes a link 52 that can be coupled to light source 12 with coupling assembly 53. At the opposite end of link 52 is a lighting element 60 positionable in working channel 24 of retractor 14. Coupling assembly 53 can include an end member 54 coupled to the end of link 52 and through which one or more light transmitting elements extend. A fitting 56 can be engaged to end member 54, and a light source connector 58 positioned over fitting 56 and secured to end member 54. Light source connector 58 is engageable to light source 12 so that light from light source 12 can be directed into light transmitting elements housed by link 52. It is also contemplated that coupling assembly 53 could include any other configuration suitable for securing link 52 to light source 12 such that light can be transmitted from light source 12 through link 52.

FIG. 3 provides a distal end view of lighting element 60 and FIG. 4 provides a cross-section through retractor 14 and looking proximally at lighting element 60 of light instrument 50 positioned therein. Lighting element 60 includes a body having an inner wall member 62 and an outer wall member 64. A passage 68 is formed between inner wall member 62 and outer wall member 64. Inner wall member 62 and outer wall member 64 can be coupled to one another at their lateral edges 74, 76 while passage 68 includes a plurality of light transmitting elements 66 therein.

Light transmitting elements 66 extend from link 52 adjacent proximal end 70 of lighting element 60 and fan out into passage 68 as shown in FIG. 1. Light transmitting elements 66 are configured relative to lighting element 60 in a manner that spaces transmitting elements 66 along passage 68 adjacent distal end 72. Passage 68 is open along at least a portion of distal end 72 to expose the distal ends of light transmitting elements 66 to the surgical space. Light transmitting elements 66 emit light from their distal ends to illuminate the surgical space. Since light transmitting elements 66 are distributed along inner wall surface 30 of retractor 14, the light emitted from the ends of light transmitting elements 66 provides effective illumination of the working space 26, and obscuring or shadowing of light by surgical instruments in working channel 24 is minimized or eliminated.

Body 18 of retractor 14 includes an inner wall surface 30 and an outer wall surface 32. Lighting element 60 is positioned in working channel 24 such that outer wall member 64 is positioned adjacent inner wall surface 30. The distal ends of light transmitting elements 66 can be dispersed at least partially around the inner wall surface 30 of body 18 to provide greater illumination of the surgical space and vary directions of emitted light. In one embodiment, light transmitting elements 66 extend around 50 percent or more of the inner perimeter of retractor body 18. In one form, light transmitting elements 66 are spaced along about 50 percent to about 75 percent of the inner perimeter of retractor 18 formed by inner wall surface 30. Other embodiments contemplated arrangements for light transmitting elements 68 that extend from about 1 percent to about 100 percent of the inner perimeter of retractor body 18, from about 25 percent to about 75 percent of the inner perimeter of retractor body 18, and from about 40 percent to 60 percent of the inner perimeter retractor body 18.

Lighting element 60 can be deformable or manipulated to various configurations by moving the lateral edges 74, 76 as indicated by arrows 78. In this manner, lighting element 60 can be altered, if needed, to conform with inner wall surface 30 of body 18. For example, lighting element 60 can be reduced in size and positioned in working channel 24 by moving lateral edges 74, 76 toward one another. Once inserted in working channel 24, edges 74, 76 can be returned toward their original configuration, if necessary, causing outer wall member 64 to contact inner wall surface 30 in frictional engagement therewith.

Lighting element 60 can be moved axially, as indicated by arrow 80 of FIG. 1, to adjust the positioning of lighting element 60 in working channel 24 while maintaining frictional engagement with the inner wall surface 30 of retractor 14. Lighting element 60 can also be rotated about inner wall surface 30, as indicated by arrow 82, to adjust the positioning of light transmitting elements 68 about working channel 24 while maintaining frictional engagement with inner wall surface 30. By providing a readily adjustable lighting element that maintains engagement with retractor 14 during adjustment, the surgeon can reposition the location and direction of the emitted light as needed without removing lighting element 60 from working channel 24, or without the risk of lighting element 60 falling into the surgical space. Other embodiments contemplate that lighting element 60 could be immovably positioned in working channel 24.

Lighting element 60 can have a shape that corresponds to the shape of working channel 24, and thus the working channel remains substantially unobstructed by lighting element 60. Surgical instruments, implants and the like can be positioned through the passage defined by inner wall member 62 while lighting element 60 remains engaged with body 18 in working channel 24 to illuminate the surgical space. Further, the radially dispersed light transmitting elements 66 provide a multitude of directions and locations from which light can be emitted, reducing the chance of completely or substantially obstructing the emitting light during the surgical procedure.

In one particular embodiment, lighting element 60 is comprised of a pair of stainless steel plates positioned along opposite sides of light transmitting elements 68, which are provided in the form of plastic optical fibers. In another embodiment, wall members 62, 64 are comprised of opaque material to prevent passage of light therethrough so it is focused through the distal ends of light transmitting elements 66. Other embodiments contemplate lighting element 60 is made from other material, such as plastic material or other metals and metal alloys, for example. It is further contemplated that lighting element 60 could be cylindrical in shape and adapted to frictionally engage the inner wall surface of the retractor. It is also contemplated that lighting element 60 could be coupled to the proximal end of the retractor via a hook-like member, set screw, or other coupling device.

Light source 12 can be any device capable of generating and/or transmitting light to link 52. Link 52 can be any one or combination of fiber optic cables, including plastic fiber optic cables, wires or other transmission device or devices capable of transmitting light between light source 12 and retractor 14. Optical fibers can be bundled in a protective sheath.

Retractor 14 is shown as a cylindrical retractor with a circular cross-section. However, other retractor embodiments are contemplated, including retractors with non-circular cross-sections, and working channels that are not completely enclosed by body 18. Other retractor examples are provided in U.S. patent application Ser. No. 09/815,693, filed Mar. 23, 2001, now U.S. Pat. No. 6,679,833; U.S. patent application Ser. No. 10/117,440, filed Apr. 25, 2002, now U.S. Pat. No. 7,261,688; and U.S. patent application Ser. No. 10/180,658, filed Jun. 26, 2002, now U.S. Pat. No. 6,945,933, each of which is incorporated herein by reference in its entirety.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical instrument for accessing and illuminating a space within a body of a patient, comprising:
   a retractor positionable with the body of the patient and including an inner wall surface defining a working channel therealong; and
   a lighting element including at least one wall member and at least one light transmitting element along said at least one wall member, said at least one wall member being deformable to assume any one of a number of configurations for positioning of the wall member in the working channel such that the wall member frictionally engages said inner wall surface, said frictional engagement sufficient to maintain a position of said lighting element relative to said retractor after said lighting element is moved while frictionally engaging said inner surface to said position, wherein said retractor is a tube with the inner wall surface of said tube defining said working channel, and said at least one wall member of said lighting element extends around more than 50 percent of said inner wall surface of said tube.

2. The instrument of claim 1, wherein said at least one light transmitting element includes a plurality of light transmitting elements extending along and spaced about said at least one wall member.

3. The instrument of claim 2, wherein said at least one wall member includes an inner wall member and an outer wall member, said plurality of light transmitting elements being positioned in a passage between said inner wall member and said outer wall member.

4. The instrument of claim 2, wherein said plurality of light transmitting elements comprise optical fibers.

5. The instrument of claim 1, wherein said at least one wall member is bendable to conform to said inner wall surface.

6. The instrument of claim 1, wherein said lighting element is movable axially along said inner wall surface while said at least one wall member maintains frictional engagement therewith.

7. The instrument of claim 1, wherein said lighting element is movable circumferentially along said inner wall surface while said at least one wall member maintains frictional engagement therewith.

8. The instrument of claim 1, wherein said at least one wall member includes a first wall member including a convexly curved surface positionable along said inner wall surface of said retractor and a second wall member including a concavely curved wall surface opposite said convexly curved wall surface, wherein said concavely curved wall surface is exposed to said working channel.

9. The instrument of claim 8, wherein said concavely curved wall surface forms a passage that parallels said working channel.

10. The instrument of claim 8, wherein said first and second wall members extend between opposite lateral edges.

11. The instrument of claim 10, wherein said first and second wall members are coupled to one another along said opposite lateral edges.

12. The instrument of claim 10, wherein said first and second wall members extend along more than 50 percent of said inner wall surface between said opposite lateral edges.

13. The instrument of claim 10, wherein said first and second wall members are comprised of opaque material.

14. The surgical instrument of claim 1, wherein said at least one wall member includes a pair of wall members forming a passage therebetween and said at least one light transmitting element is positioned in said passage, said passage opening at distal and proximal ends of said pair of wall members and said pair of wall members extend between opposite lateral edges of said pair of wall members, said pair of wall members being coupled to one another along said opposite lateral edges.

15. A surgical instrument for accessing and illuminating a space within a body of a patient, comprising:
   a retractor positionable with the body of the patient and including an inner wall surface defining a working channel therealong; and
   a lighting element including at least one wall member and at least one light transmitting element along said at least one wall member, said at least one wall member being bendable to conform with said inner wall surface and resilient to normally return toward a pre-bent configuration to frictionally engage said inner wall surface when said lighting element is positioned against said inner wall surface, said frictional engagement sufficient to maintain a position of said lighting element relative to said retractor after said lighting element is moved while frictionally engaging said inner surface to said position, wherein said retractor is a tube with the inner wall surface of said tube defining said working channel, and said at least one wall member of said lighting element extends around more than 50 percent of said inner wall surface of said tube.

16. The instrument of claim 15, wherein said at least one light transmitting element includes a plurality of light transmitting elements extending along and spaced about said at least one wall member.

17. The instrument of claim 16, wherein said at least one wall member includes an inner wall member and an outer wall member, said plurality of light transmitting elements being positioned in a passage between said inner wall member and said outer wall member.

18. The instrument of claim 15, wherein said lighting element is movable axially along said inner wall surface while said at least one wall member maintains frictional engagement therewith.

19. The instrument of claim 15, wherein said lighting element is movable circumferentially along said inner wall surface while said at least one wall member maintains frictional engagement therewith.

20. The instrument of claim 15, wherein said at least one wall member includes a first wall member including a convexly curved surface positionable along said inner wall surface of said retractor and a second wall member including a concavely curved wall surface opposite said convexly curved wall surface, wherein said concavely curved wall surface is exposed to said working channel.

21. The instrument of claim 20, wherein said first and second wall members extend between opposite lateral edges.

22. The instrument of claim 21, wherein said first and second wall members extend along more than 50 percent of said inner wall surface between said opposite lateral edges.

23. The surgical instrument of claim 15, wherein said at least one wall member includes a pair of wall members forming a passage therebetween and said at least one light transmitting element is positioned in said passage, said passage opening at distal and proximal ends of said pair of wall members and said pair of wall members extend between opposite lateral edges of said pair of wall members, said pair of wall members being coupled to one another along said opposite lateral edges.

24. A surgical instrument for accessing and illuminating a space within a body of a patient, comprising:
  a retractor positionable with the body of the patient and including an inner wall surface defining a working channel therealong; and
  a lighting element including at least one wall member and at least one light transmitting element along said at least one wall member, said at least one wall member being deformable from a first configuration to conform with said inner wall surface and configured to normally return toward said first configuration to frictionally engage said inner wall surface, wherein said lighting element is movable axially along said inner wall surface of said retractor for repositioning said lighting element in said working channel while maintaining frictional engagement with said inner wall surface, wherein said retractor is a tube with the inner wall surface of said tube defining said working channel, and said at least one wall member of said lighting element extends around more than 50 percent of said inner wall surface of said tube.

25. The instrument of claim 24, wherein said at least one light transmitting element includes a plurality of light transmitting elements extending along and spaced about said at least one wall member.

26. The instrument of claim 25, wherein said at least one wall member includes an inner wall member and an outer wall member, said plurality of light transmitting elements being positioned in a passage between said inner wall member and said outer wall member.

27. The instrument of claim 24, wherein said lighting element is movable circumferentially along said inner wall surface while said at least one wall member maintains frictional engagement therewith.

28. The instrument of claim 24, wherein said at least one wall member includes a first wall member including a convexly curved surface positionable along said inner wall surface of said retractor and a second wall member including a concavely curved wall surface opposite said convexly curved wall surface, wherein said concavely curved wall surface is exposed to said working channel.

29. The instrument of claim 28, wherein said first and second wall members extend between opposite lateral edges.

30. The instrument of claim 29, wherein said first and second wall members extend along more than 50 percent of said inner wall surface between said opposite lateral edges.

31. The surgical instrument of claim 24, wherein said at least one wall member includes a pair of wall members forming a passage therebetween and said at least one light transmitting element is positioned in said passage, said passage opening at distal and proximal ends of said pair of wall members and said pair of wall members extend between opposite lateral edges of said pair of wall members, said pair of wall members being coupled to one another along said opposite lateral edges.

* * * * *